US012758094B2

(12) United States Patent
Hernandez-Castaneda et al.

(10) Patent No.: US 12,758,094 B2
(45) Date of Patent: Oct. 13, 2026

(54) METHOD FOR QUANTIFYING OCULAR DOMINANCE OF A SUBJECT AND APPARATUS FOR IMPLEMENTING A METHOD FOR QUANTIFYING OCULAR DOMINANCE OF A SUBJECT

(71) Applicant: Essilor International, Charenton le Pont (FR)

(72) Inventors: Martha Hernandez-Castaneda, Charenton-le-Pont (FR); Paul Vernerey, Charenton-le-Pont (FR); Gildas Marin, Charenton-le-Pont (FR)

(73) Assignee: Essilor International, Charenton le Pont (FR)

( * ) Notice: Subject to any disclaimer, the term of this patent is extended or adjusted under 35 U.S.C. 154(b) by 691 days.

(21) Appl. No.: 17/759,020

(22) PCT Filed: Jan. 19, 2021

(86) PCT No.: PCT/EP2021/051071
§ 371 (c)(1),
(2) Date: Jul. 18, 2022

(87) PCT Pub. No.: WO2021/148406
PCT Pub. Date: Jul. 29, 2021

(65) Prior Publication Data
US 2023/0036885 A1 Feb. 2, 2023

(30) Foreign Application Priority Data
Jan. 20, 2020 (EP) .................................... 20305043

(51) Int. Cl.
*A61B 3/032* (2006.01)
*A61B 3/08* (2006.01)

(52) U.S. Cl.
CPC ................ *A61B 3/032* (2013.01); *A61B 3/08* (2013.01)

(58) Field of Classification Search
CPC ...... A61B 3/032; A61B 3/08; A61B 3/00–185
USPC .................................................. 351/200, 201
See application file for complete search history.

(56) References Cited

U.S. PATENT DOCUMENTS

| | | | | |
|---|---|---|---|---|
| 7,946,707 | B1 | 5/2011 | McDonald, II et al. | |
| 9,706,910 | B1 | 7/2017 | Blaha et al. | |
| 11,007,109 | B1 * | 5/2021 | Hofeldt | A61H 5/005 |
| 2008/0259277 | A1 * | 10/2008 | Inagaki | A61B 3/032 351/232 |

(Continued)

FOREIGN PATENT DOCUMENTS

WO WO 2015/179539 A1 11/2015

OTHER PUBLICATIONS

International Search Report mailed on Apr. 7, 2021 in PCT/EP2021/051071 filed on Jan. 19, 2021 (3 pages).

*Primary Examiner* — Bumsuk Won
*Assistant Examiner* — Alex Park Rickel
(74) *Attorney, Agent, or Firm* — Oblon, McClelland, Maier & Neustadt, L.L.P.

(57) ABSTRACT

An apparatus for quantifying ocular dominance of a subject, including at least one display for providing a first image representing a first target to a first eye of the subject, and for providing a second image representing a second target to a second eye of the subject, and a control unit to control the at least one display.

16 Claims, 5 Drawing Sheets

(56) References Cited

U.S. PATENT DOCUMENTS

| | | | | |
|---|---|---|---|---|
| 2009/0290122 | A1* | 11/2009 | Hosoi | A61B 3/032<br>351/201 |
| 2016/0128893 | A1* | 5/2016 | Ooi | A61B 3/08<br>351/201 |
| 2017/0065168 | A1* | 3/2017 | Bex | G02B 27/017 |
| 2017/0079524 | A1 | 3/2017 | Bex | |
| 2017/0164822 | A1* | 6/2017 | Kalder | A61B 3/0041 |
| 2017/0340200 | A1 | 11/2017 | Blaha et al. | |
| 2021/0076930 | A1 | 3/2021 | Blaha et al. | |

* cited by examiner

METHOD FOR QUANTIFYING OCULAR DOMINANCE OF A SUBJECT AND APPARATUS FOR IMPLEMENTING A METHOD FOR QUANTIFYING OCULAR DOMINANCE OF A SUBJECT

FIELD

The present description relates to a method for quantifying ocular dominance of a subject and apparatus for implementing a method for quantifying ocular dominance of a subject.

BACKGROUND

The prescription and manufacture of a pair of spectacles may be split into six main operations:

- acquiring patient related parameters;
- calculating the shapes of the optical faces of the lenses, depending on these acquired parameters;
- molding and machining of the optical faces of the lenses;
- acquiring data relating to the spectacle frame selected by the patient, including, in particular, the shapes of the outlines of the rims of this frame;
- centering the ophthalmic lenses, which consists in suitably positioning the outlines of the rims on each lens so that, once they have been machined to the shape of these outlines and then mounted in the frame, these lenses fulfill, as well as can be expected, the optical functions for which they were designed; and
- shaping the lenses.

Currently, in order to improve the visual comfort of patients, there are some researches to optimize the prescription and the optical shapes and performance of lenses, especially those of lenses exhibiting a progressive power variation (commonly called “progressive lenses”), and to improve how well they are centered in the rims of the spectacle frame.

To do this, an increasing number of patient related parameters must be taken into consideration.

Among these parameters, it is now sought to determine the dominant eye (or “master eye”) of the patient, especially in order to personalize the prescription and/or the calculation and machining of the lenses of the patient.

In this description, the “dominant eye” or “ocular dominance” is the sensory dominant eye, which refers to the eye that dominates in a conflict situation when different visual stimulations are seen by each eye.

Various empirical methods are known for determining the dominant eye of the patient, which, in practice, prove to be unreliable since they are based entirely on the skill and ease with which the patient can implement them.

One very common method is the “hole-in-card” method also called the “hole-in-the-card test” or the Dolman method.

This method proves to be one of the surest ways of identifying the dominant eye of an individual. It consists in:

- giving the patient a card with a hole in its center;
- asking the patient to hold this card in both hands, with straight arms; and then in
- asking the patient to keep both eyes open and to sight a target, located at a distance in front of them, through the hole (in the sighting position the subject perceives the target centered in the hole).

The patient then closes each of his/her eyes in alternation in order to identify their dominant eye, which, in practice, is the eye aligned with the target and the hole. Thus, if the target is still centered in the hole when the patient shuts their left eye, their right eye is dominant. Conversely, if the target is still centered in the hole when they shut their right eye, their left eye is dominant. This method allows the dominant eye to be determined but not to quantify ocular dominance.

However, quantifying ocular dominance may be a key point to personalize accurately the prescribed correction and/or the calculation and the machining of the lenses of the patient. Thus it allows obtaining an accurate balance between the eyes possibly for all viewing distances (from near vision to far vision) which is necessary for a good and comfortable binocular vision.

SUMMARY

In order to meet this need, the present description provides an apparatus and a method for quantifying ocular dominance of a subject. In particular, it is a subjective method to evaluate and adjust the binocular balance between the eyes. It allows quantifying ocular dominance and balancing finely the correction between the two eyes (the spherical refractive balance between eyes).

One object of the disclosure is to provide a method and an apparatus, for quantifying accurately the ocular dominance of a subject possibly for all viewing distances (from near vision to far vision), in which bad effects, caused by rivalry and/or by suppression phenomenon, are avoided or at least reduced.

The above object is achieved according to the invention by providing an apparatus for quantifying ocular dominance of a subject comprising at least one display for providing a first image representing a first target to a first eye of the subject, and for providing a second image representing a second target to a second eye of the subject, and a control unit to control the at least one display. The first image and the second image are such that the first target on the first image has an identical position, an identical orientation, an identical size and an identical shape to the second target on the second image. The first target comprises n points (PL1,. . ., PLi, . . . PLj, . . . PLn) and the second target comprises n points (PR1, . . . , PRi, . . . PRi PRn) where $n \geq 2$, $1 \leq i \leq n$ and $1 \leq j \leq n$; each point (PLi) of the first target matches with a point (PRi) of the second target where PLi has the same position in the first image than PRi for 1 in the second image. To each point (PLi) of the first target and to each point (PRi) of the second target corresponds respectively a feature value VLi for the first target and a feature value VRi for the second target. The feature value of at least two points (PLi, PLj) of the first target differs; and for each n points (PLi, PRi) of the first and second target $VLi+VRi=VLj+VRj$ for any i and j.

One explanation for this improvement is that, as the visual system of the subject sees a first image and a second image that are mostly similar, it perceives no contradiction between the first and second images and, thus, does not perform any selection between one or the other of the left and right visual pathways of the subject. Thus, the subject sees a fused image from the first image and the second image. The target of the fused image may be an identical position, an identical orientation, an identical size and an identical shape to the target of the first and the second images; but may have different feature values than the target of the first and the second images.

For example, each points of the targets may be a pixel of the at least one display.

According to an advantageous, optional feature, the apparatus comprises means to vary the feature values of the first and/or the second target. Thanks to this embodiment, it is possible to quantify the dominant eye by varying the feature values of the first and/or the second target until the subject does not see the contrast in the fused image from the first and the second image, in other words does not see the target in the fused image. Indeed, when the contrast disappear in the fused image, it is possible from the ratio between the feature values of the first and the second target to quantify the dominant eye.

According to an advantageous, optional feature, the apparatus comprises a first optical unit and a second optical unit respectively in front of the first eye and in front of the second eye of the subject. The optical unit may be a set of lens. The apparatus may also comprise a power modulator to change the optical power of the optical unit in front of each eye such as a blurring lens or any device able to modify the optical power. Thanks to this embodiment of the apparatus, the dominant eye is blurred, that is to say fogged, by adding additional positive or negative diopters to a starting correction. Then, this eye is defogged step by step until the subject does not see the contrast in the fused image from the first and the second image, in other words until he does not see the target in the fused image. When the contrast disappears in the fused image, it means that the inversion of the dominance between the both eyes occurs which indicates a dominance breakpoint. The dominance breakpoint appears to be a useful quantitative indicator of the dominance of the eye in clinical applications. Also, advantageously, this embodiment aims to neutralize the tendency to accommodate. Accommodation is a trap that should be avoided, especially in children but also in adults. Because it masks a farsightedness and exposes to the risk of prescribing an inappropriate correction if one neglects its role during the examination.

According to an advantageous, optional feature, the feature values of the target are the luminosity or the color.

According to an advantageous, optional feature, the feature value of at least three points of the first target differs.

According to an advantageous, optional feature, the first and the second target are surrounded with a peripheral area. The inventors have observed that providing the two eyes of the subject with two images that comprise identical or similar peripheral images, induces a well-balanced fusion of the left and right visual pathways. It results, for the subject, in a perceived image that is stable.

According to an advantageous, optional feature, the shape of the targets is an element grid comprising at least three elements, the at least three elements having the same shape and the same size; or an element line comprising at least three elements, the at least three elements having the same shape and the same size; or an element column comprising at least three elements, the at least three elements having the same shape and the same size; or at least two fringes or; letter(s) or optotype(s) or figure(s).

According to an advantageous, optional feature, each element has the same feature value at each point of the element. This embodiment presents a better performance because it seems easier to the subject to express about the localization of the perception of the feature values.

According to an advantageous, optional feature, the control unit comprises an adaptive algorithm executed by the control unit, the adaptive algorithm being configured to accept a report describing how the subject sees when presented the first image and the second image, and to calculate adjustments to the feature values of the first and/or second target on the first image and the second image to be presented in a next iteration of the first image and the second image according to the report; a target generating component configured to provide the next iteration of the first image and the second image to the subject. This adaptive algorithm makes the apparatus and the method more efficient and faster.

According to an advantageous, optional feature, the control unit comprises an adaptive algorithm executed by the control unit, the adaptive algorithm being configured to accept a report describing how the subject sees when presented the first image and the second image, and to calculate adjustments of the optical power of the optical units in a next iteration of the first image and of the second image according to the report. This adaptive algorithm makes the apparatus and the method more efficient and faster.

Alternatively, the control unit may comprise an algorithm to accept a report describing how the subject sees when presented the first image and the second image, and to calculate adjustments of the optical power of the optical units and to calculate the feature values in a next iteration of the first image and of the second image according to the report.

According to an advantageous, optional feature, the fused image is a 3-D stereoscopic image.

One object of the disclosure is to provide a refractometer comprising an apparatus as described in the present disclosure. Such refractometer presents the advantage to allow the correction of the dominant eye as consideration for correction related to refractive errors.

One object of the disclosure is a set of images for quantifying the ocular dominance of a subject, comprising a first image representing a first target and a second image representing a second target. The first image and the second image are such that the first target on the first image has an identical position, an identical orientation, an identical size and an identical shape to the second target on the second image. The first target comprises n points (PL1, . . . , PLi, . . . . . . PLj, . . . PLn) and the second target comprises n points (PR1, . . . , PRi, . . . , PRj . . . PRn) where $n \geq 2$, $1 \leq i \leq n$ and $1 \leq j \leq n$; each point (PLi) of the first target matches with a point (PRi) of the second target where PLi has the same position in the first image than PRi for in the second image. To each point (PLi) of the first target and to each point (PRi) of the second target corresponds respectively a feature value VLi for the first target and a feature value VRi for the second target. The feature value of at least two points (PLi, PLj) of the first target differs; and for each n points (PLi, PRi) of the first and second target VLi+VRi=VLj+VRj for any i and j.

One object of the disclosure is to provide a method for quantifying ocular dominance according to claims 9 to 13 and a method for adjusting a binocular balance of a subject according to claims 14 to 15.

According to the present disclosure, the method for quantifying ocular dominance of a subject comprises

- providing a first image to a first eye of the subject, the first image representing a first target,
- providing a second image to a second eye of the subject, the second image representing a second target.

The first image and the second image are such that the first target on the first image has an identical position, an identical orientation, an identical size and an identical shape to the second target on the second image. The first target comprises n points (PL1, . . . , PLi, . . . . PLj, . . . PLn) and the second target comprises n points (PR1, . . . , PRi, . . . , PRj . . . PRn) where $n \geq 2$, $1 \leq i \leq n$ and $1 \leq j \leq n$. Each point (PLi) of the first target matches with a point (PRi) on the second target where PLi has the same position in the first image than PRi for $1 \leq i \leq n$ in the second image. To each point (PLi) of the first target and to each point (PRi) of the second target corresponds respectively a feature value VLi for the first target and a feature value VRi for the second target. The feature value of at least two points (PLi, PLj) of the first target differs; and for each n points (PLi, PRi) of the first and second target VLi+VRi=VLj+VRj for any i and j. Then the method comprises the steps to checking that the subject sees a fused image from the first image and the second image, the fused image comprising a fused target with feature values;

generating a first report describing the features values of the fused image;

determining which eye is the dominant eye of the subject based on the report.

By checking, we mean to obtain the feedback of the subject if he sees a fused image similar to the first image. The feedback may be implicit or explicit.

According to an embodiment, the method comprises further after determining which eye is the dominant eye of the subject:

calculating adjustments to the feature values (VLi, VRi) of the first and/or second target on the first image and the second image to be presented in a next iteration of the first image and the second image according to the report;

providing the next iteration of the first image (20L, 30L) and the second image with the adjusted feature values;

generating a second report describing how the subject sees the features values of the fused target from the next iteration of the first image and of the second image;

performing the precedent steps until the subject indicates that according to its perception, the feature values of the fused target of the fused image are constant at each point of the fused target of the fused image;

quantifying ocular dominance of the subject based on the reports of the subject.

According to an embodiment, the shape of the targets is a set of at least three elements, said at least three elements having the same shape and the same size. The feature values of the target are the luminosity, and the reports describe the location of the brightest and/or darkest element of the fused target of the fused image.

According to an embodiment, the target is a set of at least three elements, said at least three elements having the same shape and the same size. The feature values of the target are the colors of the target, $$VLi+VRi=VLj+VRj$$

meaning that VLi (VRi) corresponds to a first color and VLj (VRj) corresponds to a second color which is the complementary color of the first color. The reports describe the location of the colors on the fused target of the fused image.

According to an embodiment, the fused image is a 3-D stereoscopic image.

One object of the disclosure is to provide a method for adjusting a binocular balance of a subject comprising providing a first image to a first eye of the subject, the first image representing a first target, providing a second image to a second eye of the subject, the second image representing a second target.

The first image and the second image are such that the first target on the first image has an identical position, an identical orientation, an identical size and an identical shape to the second target on the second image. The first target comprises n points (PL1, . . . , PLi, . . . PLj, . . . PLn) and the second target comprises n points (PR1, . . . , PRi, . . . , PRj . . . PRn) where n≥2, 1≤i≤n and 1≤j≤n. Each point (PLi) of the first target matches with a point (PRi) on the second target where PLi has the same position in the first image than PRi for 1<i<n in the second image. To each point (PLi) of the first target and to each point (PRi) of the second target corresponds respectively a feature value VLi for the first target and a feature value VRi for the second target. The feature value of at least two points (PLi, PLj) of the first target differs; and for each n points (PLi, PRi) of the first and second target VLi+VRi=VLj+VRj for any i and j. Then the method comprises the steps to checking that the subject sees a fused image from the first image and the second image, the fused image comprising a fused target with feature values;

generating a report describing the features values of the fused image;

determining which eye is the dominant eye of the subject based on the report;

providing a correction to the dominant eye of the subject by adjusting a power lens in front of the first eye and/or the second eye until the feature values of the fused image seems constant for the subject.

According to an embodiment, the method for adjusting a binocular balance of a subject comprises:

measuring the refraction of each eye of the subject;

providing a correction based on the measured refraction by adjusting a power lens in front of the first eye and/or the second eye.

According to an embodiment, the steps of measuring the refraction of each eye and providing a correction based on the measured refraction may be realized before to providing a first image or after to providing a correction to the dominant eye.

According to an advantageous, optional feature, the methods comprise the step of varying the perception of the first and the second target, the sum of the feature value of the first target with the feature value of the second target is constant at each said performing. Thus, the perception of the fused target is optimized by adjusting either the feature values of the first and the second target or by adjusting a blurring lens in front of each eye of the subject.

The optional features of the apparatus presented above can also be applied to the refractometer, the set of images or the method defined respectively by claim 7, claim 8 and claims 9 to 15.

Thanks to this apparatus and the method as described in the present disclosure, the benefits may be but not exclusively:

continuous quantification of ocular dominance rather than only defining the dominant eye;

balancing finely the correction between the two eyes.

simple understanding and easy to answer for the subject (just comparing dark level instead of judging clarity of letters);

using even with low acuity level;

using before/after a binocular/monocular refraction, during a standard bi-ocular step instead of using letters or in itself to quantify the level of dominance adaptability of various parameters in the refraction result or refraction process to the level of dominance;

helping to avoid ocular rivalry and suppression.

BRIEF DESCRIPTION OF THE DRAWINGS

The following description with reference to the accompanying drawings will make it clear what the invention consists of and how it can be achieved. The invention is not limited to the embodiment/s illustrated in the drawings.

Accordingly, it should be understood that where features mentioned in the claims are followed by reference signs, such signs are included solely for the purpose of enhancing the intelligibility of the claims and are in no way limiting on the scope of the claims.

In the accompanying drawings:

FIG. 1 represents an apparatus for quantifying ocular dominance of a subject according to one example of the present description;

FIGS. 2A, 2B and 2C represent schematically a couple of images according to one embodiment of the present description, comprising a first image and a second image, to be provided respectively to the right eye and the left eye of the subject by the apparatus of FIG. 1, and an image which is the sum of the first and the second image;

FIGS. 3A, 3B and 3C represent three images according to an embodiment of the present description comprising a first image and a second image to be provided respectively to the right eye and the left eye of the subject by the apparatus of FIG. 1, and an image which is the sum of the first and the second image;

FIGS. 4A, 4B and 4C represent three images according to an embodiment of the present description comprising a first image and a second image to be provided respectively to the right eye and the left eye of the subject by the apparatus of FIG. 1, and an image which is the sum of the first and the second image;

FIGS. 5A, 5B and 5C represent three images according to an embodiment of the present description comprising a first image and a second image to be provided respectively to the right eye and the left eye of the subject by the apparatus of FIG. 1, and an image which is the sum of the first and the second image;

FIGS. 6A, 6B and 6C represent three images according to an embodiment of the present description comprising a first image and a second image to be provided respectively to the right eye and the left eye of the subject by the apparatus of FIG. 1, and an image which is the sum of the first and the second image;

FIGS. 7A, 7B and 7C represent three images according to an embodiment of the present description comprising a first image and a second image to be provided respectively to the right eye and the left eye of the subject by the apparatus of FIG. 1, and an image which is the sum of the first and the second image;

Figure 8C:
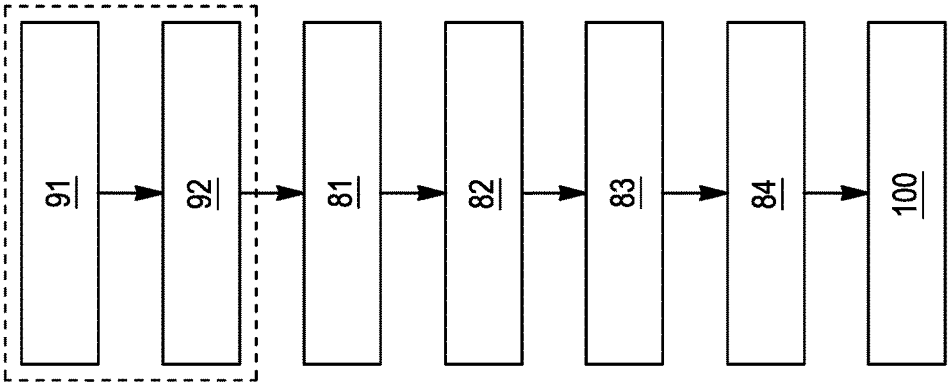
Figure 8B:
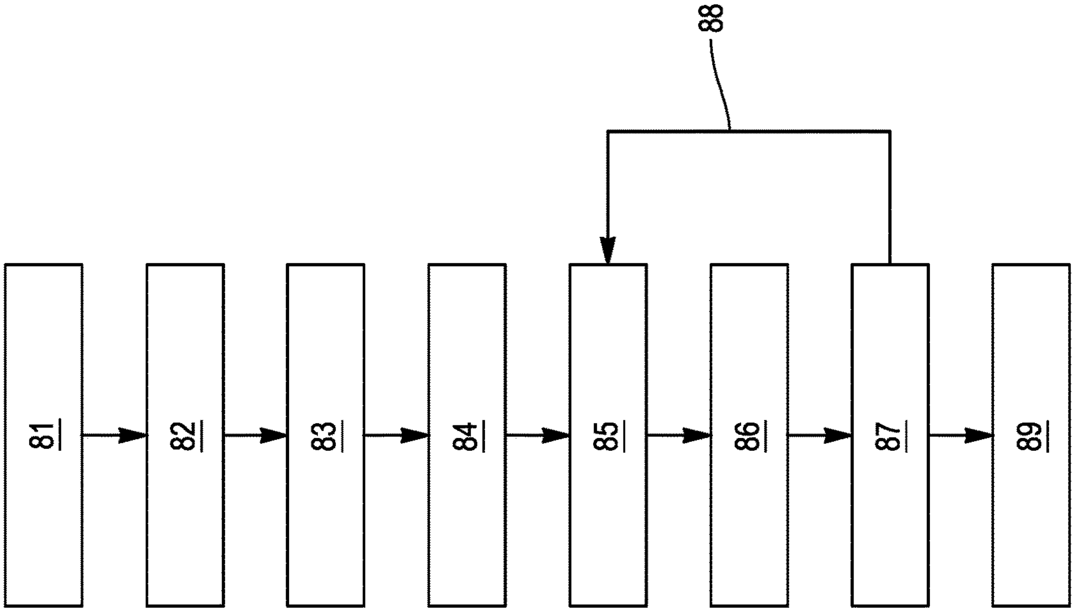
Figure 8A:
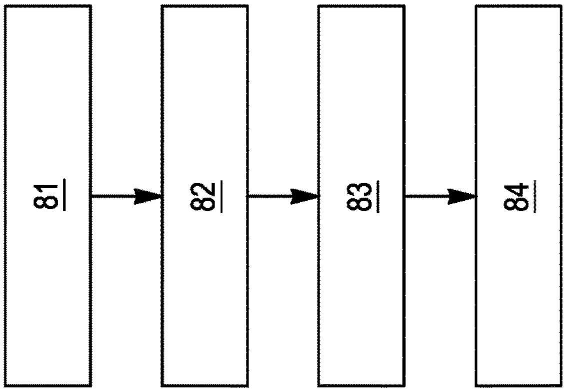

FIGS. 8A, 8B and 8C represents respectively some steps of a method for quantifying ocular dominance of a subject according to an embodiment of the present description, some steps of a method for quantifying ocular dominance of a subject according to another embodiment of the present description, some steps of a method for adjusting a binocular balance according to an embodiment of the present description.

DETAILED DESCRIPTION OF EMBODIMENTS

Figure 1:
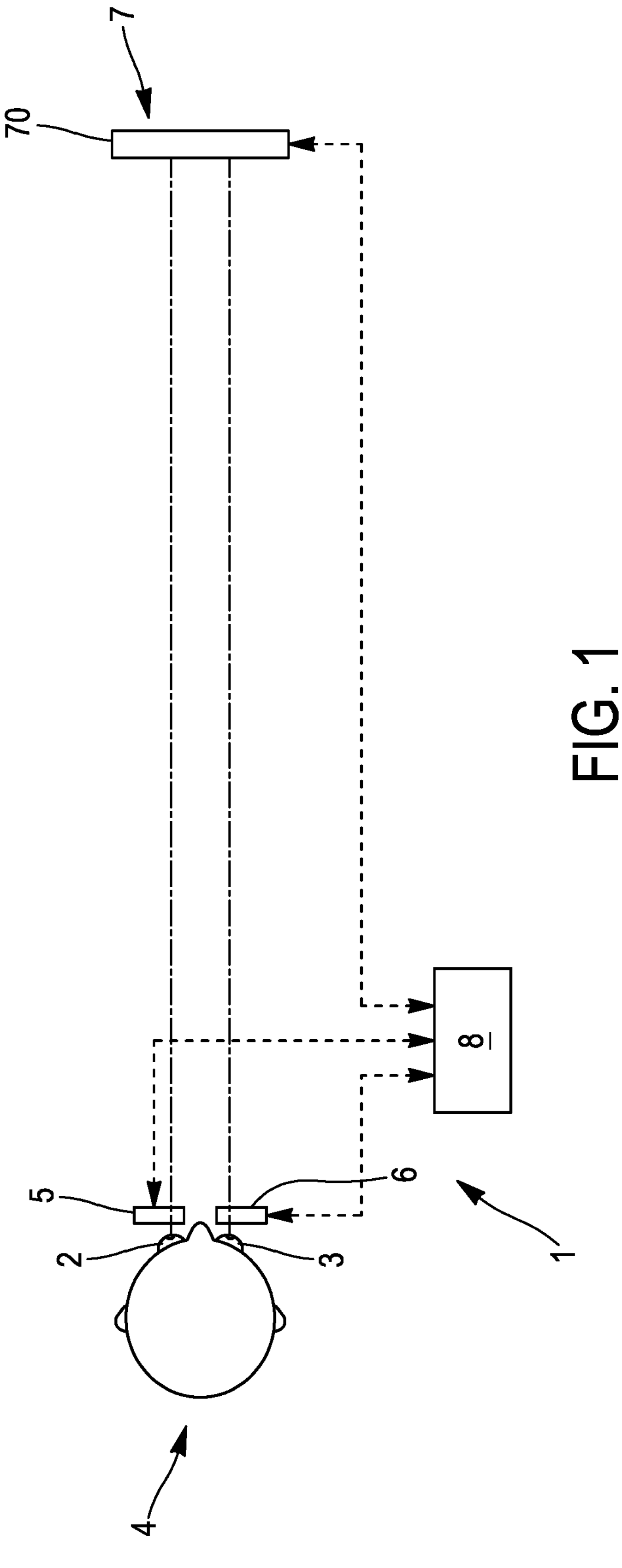

FIG. 1 represents schematically, from above, the main elements of an apparatus 1 for quantifying ocular dominance of a subject 4, in a binocular manner, that is while the subject 4 has both eyes opened and un-obstructed.

The apparatus comprises a display 7 such as an image display system, for providing a first image 20L, 30L representing a first target 22L, 32L to a first eye 2 of the subject 4, and for providing a second image 20R, 30R representing a second target 22R, 32R to a second eye of the subject 4. The first image and the second image may be provided to the subject 4 at the same time or at different time such that the subject has the perception to see the first image and the second image at the same time.

The first image 20L, 30L may be seen by the first eye 2 of the subject through a first optical unit 5 such as a set of lens, while the second image 22R, 32R may be seen by the second eye 3 of the subject 4 through a second optical unit 6 such as a set of lens.

In the embodiment of FIG. 1, each of the first and second optical units 5, 6 comprise a lens, a mirror, or a set of such optical components, that has adjustable optical power features. For instance, the lens may comprise a deformable liquid lens having an adjustable shape. Alternatively, the optical unit may comprise a set of non-deformable lenses having different optical powers, and a mechanical system that enables to select some of these lenses to group them to form the set of lenses through which the subject 4 can look. In this last case, to adjust the optical power of the set of lenses, other lenses stored in the optical unit replace one or several lenses of the set of lenses. Thus, in order to change the optical power of the optical unit 5, 6 in front of each eye 2, 3, the apparatus may comprise a power modulator, the power modulator may be controlled manually or by the control unit 8.

Each of these optical units 5, 6 is intended to be placed in front of one of the eyes 2, 3 of the subject, close to this eye (not further than a five centimeters, in practice), so that this eye 2, 3 can see a screen 70 of the display 7 through the lens, through the set of lenses, or by reflection onto a mirror of the optical unit 5, 6.

Alternatively, the subject may see the display directly without the optical unit.

The apparatus is configured to enable ocular dominance quantification at various distances (near vision, far vision and/or intermediate vision) and/or for various eye gaze directions (for example natural eye gaze direction lowered for reading, horizontal eye gaze direction for far vision). This screen 70 is located at a distance from the subject comprised between 25 cm (for near vision) and infinity when using a specific imaging system (not represented), such as a Badal system, or, if no imaging system is used (or using a plane mirror), up to about 8 meters in practice, or such as a system similar to the one disclosed in EP 3 298 952 allowing the combination of a first image provided by a screen (that could be constituted of one or more peripheral image(s)), and a second image provided by an imaging module (that could be constituted of one or more of central images), both first and second images being possibly imaged at variable distances for the individual's eye.

The lens, the set of lenses, or the set of lenses and mirrors of each of the first and second optical units 5, 6 has an overall spherical power S (spherical optical power, expressed for instance in diopters). And the cylindrical components of its refractive power are those of an equivalent cylindrical lens that has a cylindrical power C (expressed for instance in diopters), and whose cylinder has an orientation represented by an angle $\alpha$. Each of the first and second refraction correction, provided by the corresponding optical unit 5, 6, may be characterized by the values of these three refractive power parameters S, C and $\alpha$. This refractive correction could be equally characterized by the values of any other set of parameters representing the above mentioned refractive power features of the optical unit 5, 6, such as the triplet {M, J0, J45}, where the equivalent sphere M is equal to the sphere S plus half of the cylinder C ($M=S+C/2$), and where $J0=C/2*\cos(2\alpha)$ and $J45=C/2*\sin(2\alpha)$ are the refractive powers of two Jackson crossed cylinders lenses representative of the cylindrical refractive power features of the lens or of the set of lenses of the optical unit 5, 6.

According to an embodiment of the present description, the lens, the set of lenses, or the set of lenses of the first and second optical units 5, 6 may be blurring lens which are spherical, in other words C=0.

Regarding now the display 7, the display may comprise a screen 70.

The whole extent of the screen 70 may be seen through each of the first and second optical units 5, 6.

The display 7 may be realized by means of a liquid-crystal display screen 70 that is able to display the first image 20L, 30L with a first polarization, and, at the same time, to display the second image 20R, 30R with a second polarization. The first and second polarizations are orthogonal to each other. For instance, the first and second polarizations are both rectilinear and perpendicular to each other. Or, similarly, the first polarization is a left-hand circular polarization while the second polarization is a right-hand circular polarization.

The first optical unit 5 in front of the first eye may comprise a first polarizing filter that filters the light coming from the image display system 7. The first polarizing filter filters out the second polarization, and lets the first polarization pass through so that it can reach the first eye 2 of the subject. So, through the first polarizing filter, the first eye 2 of the subject can see the first image 20L, 30L but not the second image 20R, Similarly, the second optical unit in front of the second eye may comprise a second polarizing filter that filters the light coming from the display 7. The second polarizing filter filters out the first polarization, and lets the second polarization pass through so that it can reach the second eye 3 of the subject.

The display may use any other separation technics, such as «active» separation for which each image test is displayed alternatively at a high frequency while an electronic shutter synchronized is blocking the eye for which the image should not be addressed. Separation system could also use chromatic separation with chromatic filters both on the display and the eye in which each side/eye has different chromatic filters that block each other (for example red and green filters).

The first and second images (as represented on FIG. 2, for instance), coincide with each other (their respective frames coincide with each other), on the screen 70. They both fill the same zone, on this screen.

Here, the screen 70 may fill a part of the subject's field of binocular view that is at least 5 degrees wide, or even at least 10 degrees wide.

In alternative embodiments, the display may be implemented by means of a reflective, passive screen (such as an aluminum-foil screen) and one or several projectors for projecting onto this screen the first image, with the first polarization, and the second image, with the second polarization, the first and second images being superimposed to each other, on the screen.

Alternatively, the apparatus may comprise two displays. According to one embodiment, the first image is displayed on the first image and the second image is displayed on the second image, for instance using a Head up Virtual Reality device.

Here, the screen of the first display and the screen of the second display may fill a part of the subject's field of the monocular or binocular view that is at least 5 degrees wide, or even at least 10 degrees wide.

In alternative embodiments, the first and second displays may be achieved, for instance, by means of a first and a second Badal-like systems, placed respectively in front of the first eye, and in front of the second eye of the subject. Each of these Badal-like systems would comprise at least one lens, and a displacement system to modify a length of an optical path that joins this lens to the display screen considered, in order to form an image of this display screen at a distance from the eye of the subject that is adjustable.

Anyhow, the at least one display is controlled by a control unit 8 of the apparatus 1.

The control unit 8, that may comprises at least one processor and at least one non-volatile memory, may be programmed to control the at least one display, to vary/adjust the feature values of the first and/or the second target, and/or to control the power modulator in order to change the optical power of the optical unit 5,6.

As presented in detail below and illustrated in FIGS. 2A, 2B and 2C, the at least one display 7 provides a first image 20L, 30L representing a first target 22L, 32L to a first eye 2 of the subject 4, and provides a second image 20R, 30R representing a second target 22R, 32R to a second eye of the subject.

The first image 20L, 30L and the second image 20R, 30R are such that the first target 22L, 32L on the first image 20L, 30L has an identical position, an identical orientation, an identical size and an identical shape to the second target 22R, 32R on the second image 20R, 30R.

The first target 22L, 32L comprises n points (PL1, . . . , PLi, . . . PLj, . . . PLn) and the second target 22R, 32R comprises n points (PR1, . . . , PRi, . . . , PRj . . . PRn) where $n \geq 2$, $1 \leq i \leq n$ and $1 \leq j \leq n$. Each point (PLi) of the first target 22L, 32L matches with a point (PRi) of the second target 22R, 32R where PLi has the same position in the first image 20L, 30L than PRi for 1 in the second image 20R, 30R. To each point (PLi) of the first target and to each point (PRi) of the second target corresponds respectively a feature value VLi for the first target and a feature value VRi for the second target. The feature value of at least two points (PLi, PLj) of the first target differs; and for each n points (PLi, PRi) of the first and second target $$VLi+VRi=VLj+VRj \text{ for any } i \text{ and } j.$$

Consequently, the feature value VRi, VRj of the two points (PRi, PRj) of the second target that match with the two points (PLi, PLj) of the first target, differs.

By "identical", we mean that a level of similarity in position, orientation, size and shape between the first target and the second target is higher than a certain threshold.

It is noted however that, alternatively, the first and second target could be very similar from each other, yet not completely identical for example to enable a 3-D stereoscopic rendering of the scene represented. Still, in such a case, the first and second target would be similar enough that a level of similarity between them is higher than a given threshold.

This level of similarity could for instance be equal to a normalized correlation product between the first target and the second target, that is to say equal to the correlation product between them, divided by the square root of the product of the autocorrelation of the first target by the autocorrelation of the second target. In such a case, the level of similarity threshold mentioned above could be equal to 0.8, for instance.

The level of similarity could also be defined, between two targets similar in size/shape, as an angular deviation of less than 6° when observed by a subject at far vision distance, or as a difference of less than +/−1 diopter.

More generally, the level of similarity threshold could be equal to 0.8 times a reference level of similarity, this reference level of similarity being a level of similarity between the first target and the first image itself, computed in the same manner as the level of similarity between the first and second targets (except that it concerns the first target only).

Alternatively, the level of similarity threshold could be equal to 10 times a level of similarity computed between the first target and a random image.

The admissible range of level of similarity can be defined empirically by showing to a subject successive combination of two images with the same first reference image and different second images differing each from the first reference image and from another, and defining each with the first reference image a particular level of similarity. The lower limit of the admissible range of level of similarity will correspond to the highest level of similarity at which a subject cannot perceive a 3-D stereoscopic rendering of the scene represented. The upper limit of the admissible range of level of similarity will correspond to the lowest level of similarity at which a subject will complain of double vision or suppression.

The feature value may be the luminosity or the colors. In the case of the luminosity, the feature value of the target may correspond to a level of grey or to an intensity or an amplitude for a same color.

The feature value of at least two points (PLi, PLj) of the first target differs. The difference between the feature values defines a contrast. Advantageously, the feature value of at least three points (PLi, PLj) of the first target differs, making easier the perception of the contrast or variation between the point if dominance is unbalanced for the subject.

Figure 2C:
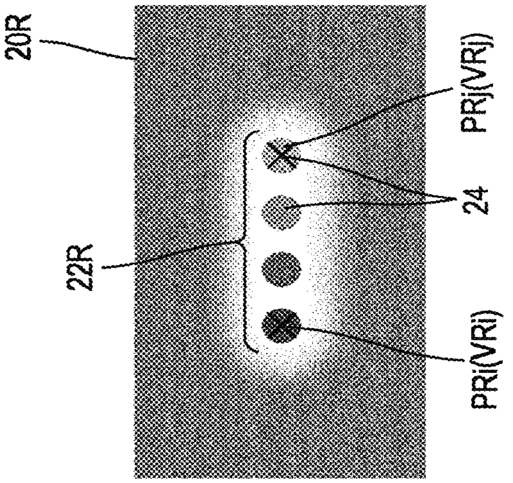
Figure 2B:
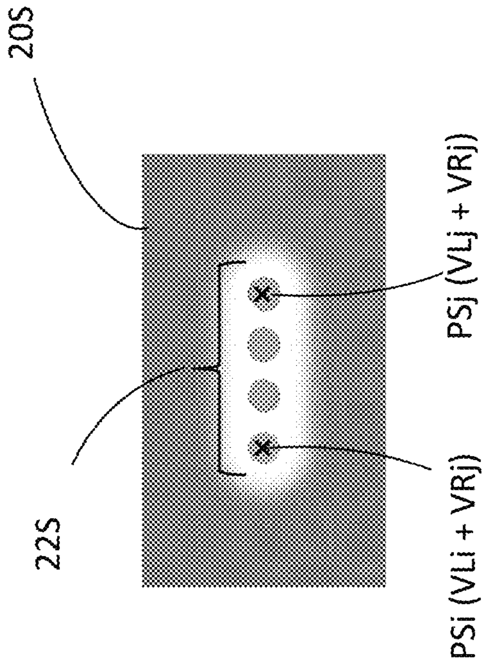
Figure 2A:
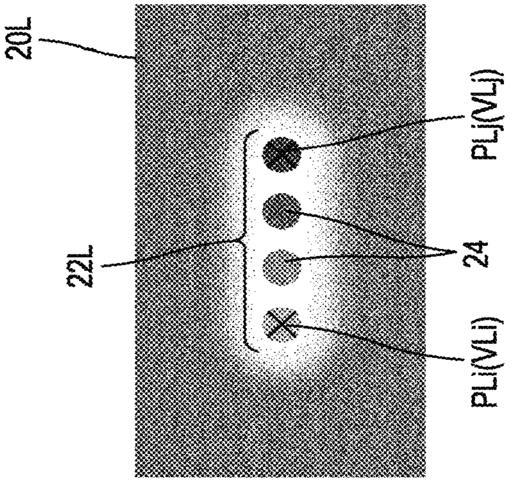

FIG. 2A illustrates the first image 20L representing a first target 22L. FIG. 2C illustrates the second image 20R representing a second target 22R. The first target 22L and the second target 22R has an identical position, an identical orientation, an identical size and an identical shape on the first image and on the second image. Indeed the first target 22L and the second target 22R are an identical element line comprising four circular elements 24 having the same size, the element line are oriented horizontally and positioned respectively in the middle of the image.

In FIGS. 2A and 2C, the first image and the second image comprise n points and the features values are the luminosity. The first image comprises the points PLi and PLj that have respectively the feature value VLi and VLj. VLi and VLj correspond to different levels of grey, in particular in FIG. 2A, PLi is bright and PLj is dark. The second images comprises the points PRi and PRj which match respectively with PLi and PLj. PRi and PRj have respectively the feature value VRi and VRj, VRi and VRj correspond to different levels of grey, in particular FIG. 2C, inversely to the first image in FIG. 2A, PRj is bright and PRi is dark.

Inside each element 24, the feature value may be constant as illustrated, for example, on FIGS. 2A, 2B and 2C.

FIG. 2B shows an image 20S representing the summed up target 22S of the feature values VL of the first target 22L with the feature value VR of the second target 22R for each n points PLi, PRi of the first and second target, in other words at each point PSi of the summed up target 22S, the feature value VSi=VLi+VRi. As shown in FIG. 2B, the level of grey is the same at each point of the summed up target 22S:

$$VLi+VRi=VLj+VRj \text{ for any } i \text{ and } j.$$

Thus, as the diagram of FIGS. 8A, 8B, 8C according three embodiments of the present disclosure illustrates the method, the first image representing the first target is provided 81 to the first eye of the subject, the second image representing the second target is provided 81 to the second eye of the subject. Thanks to the display as explained before, the subject sees a fused image from the first image and the second image representing a fused target from the first target and the second target. However, to be sure, the methods may comprise a step 82 to check if the subject sees a fused target.

The step of checking may be implicit or explicit by asking to the subject.

If the subject does not see a fused image representing a fused target from the first image and the second image, the position (between the first image and the second image or between the subject and the images) and/or the size of the first image and the second image are adjusted and/or the feature values are varied on one or both images (to adjust the balance) such that the subject sees a fused image.

If there is no dominant eye between the first eye and the second eye, the fused target of the fused image perceived by the subject may correspond to the summed up target 22S, 32S, e.g. for the subject, all the points of the fused target seem to have a constant feature value.

Alternatively, if there is a dominant eye between the first eye or the second eye, the fused target perceived by the subject may not correspond to the summed up target and the subject may see the fused target with points having different feature values. For example:

- if the first eye is dominant, the subject sees the point PSi less dark than the point PSj; or
- if the second eye is dominant, the subject sees the point PSi darker than the point PSj.

Alternatively, the feature values may be the color of the first/second target. In this case, "VLi+VRi=VLj+VRj" means that VLi corresponds to a first color and VRi to a second color which is the complementary color of the first color and similarly VLj corresponds to another first color and VRj to another second color which is the complementary color of the another first color. For example, VLi is green, VRi is red, VLj is yellow and VRj is purple. Another example, VLi is green, VRi is red, VLj is red and VRj is green. Consequently:

- If there is no dominant eye, the fused target of the fused image is uniform, in other words the subject perceived the same color on all the fused target;
- if the first eye is dominant, the subject sees the point PSi on the fused target with a color closer to the color of the point PLi; or
- if the second eye is dominant, the subject sees the point PSi on the fused target with a color closer to the color of the point PRi.

Thus, in the case where VLi is green, VRi is red, VLj is red and VRj is green:

- if there is no dominant eye, the fused target of the fused image is uniform, in other words the subject perceived all the fused target in grey;
- if the first eye is dominant, the subject sees the point PSi with a color closer to green and PSj with a color closer to red; or
- if the second eye is dominant, the subject sees the point PSj with a color closer to green and PSi with a color closer to red.

Thus, according to an embodiment of the present disclosure, based on the perception of the subject of the fused target, a report is generated (step 83 in FIGS. 8A, 8B, 8C) which describes the perception of the subject of the fused target of the fused image and accordingly, the dominant eye of the subject is determined (step 84 in FIGS. 8A, 8B, 8C).

According to an embodiment of the present disclosure, after generating the report, the feature values VLi, VRi of the first and/or the second target 22L, 32L, 22R, 32R may be adjusted (step 85 in FIG. 8B) manually or thanks to a dimmer switch, a modulator or a control unit, preferably a control unit which may vary/adjust the feature values of the first and/or the second target.

According to an embodiment of the present disclosure, for each n points (PLi, PRi) of the first and second target, the adjusted feature values VLi', VLj' of the first target and the adjusted feature values VRi', VRj' of the second target are such that $$VLi'+VRi'=VLj'+VRj' \text{ for any } i \text{ and } j.$$

This embodiment allows retrying the measurement with a different balance while respecting the initial condition.

According to another embodiment of the present disclosure, $$VLi'+VRi'=VLj'+VRj'=VLi+VRi.$$

This embodiment allows keeping global contrast constant in time which is easier for the subject to evaluate changes.

According to an embodiment of the present disclosure, the next step is to provide (step 86 in FIG. 8B) to the first eye a next iteration of the first image 20L, 30L with the adjusted/varied feature values VLi', VLj' to the first eye 2 and to provide a next iteration of the second image 20R, 30R with the adjusted/varied feature values VRi', VRj' to the second eye 3.

According to an embodiment of the present disclosure, a report describing the features values of the fused target from the next iteration of the first image and of the second image is generated (step 87 in FIG. 8B); An other words, a report describing how the subject sees the features values of the fused target from the next iteration of the first image and of the second image is generated One embodiment to quantify the ocular dominance is to perform the precedent steps several times (step 88 in FIG. 8B) until the subject indicates that according to its perception, the feature values of the target of the fused image are constant at each point of the target of the fused image. Finally, from the adjusted feature values of the last iteration for which the subject perceives constant feature values at each point of the fused target, ocular dominance of the subject is quantified (step 89 in FIG. 8B). For example the ocular dominance is quantified by making the ratio between a feature value at a point of the target of the first image presented to the dominant eye under a feature value at the matched point of the target of the second image presented to the other eye e.g. if the dominant eye is the first eye, the ratio is VLi'NRi'. With this ratio, the quality/degree of dominance ie, strong/weak dominance may be also evaluated.

Alternatively, another embodiment to quantify the ocular dominance is by adjusting binocular balance as illustrated in FIG. 8C. Thus, after determining 84 the dominant eye of the subject, a correction is provided 100 to the first eye and/or the second eye with for example a lens, preferably to the dominant eye with for example a blurring lens. Advantageously, by correcting the dominant eye with a blurring lens instead of correcting by increasing the optical power of the non-dominant eye, it allows to avoid the accommodation to be corrected and not the ocular dominance.

As for the precedent embodiment, the appropriate correction may be obtained by iteration (not illustrated in FIG. 8C). In other words, a first correction is provided to the first eye and/or the second eye. Then, according to an embodiment of the present disclosure, a report describing the features values of the fused target or in other words how the subject sees through the lens the features values of the fused target, is generated. After, the precedent steps are repeated several times with different optical power lens or different blurring lens until the subject indicates that according to its perception, the feature values of the target of the fused image are constant at each point of the target of the fused image. Finally, from the optical power or the blurring lens, ocular dominance of the subject is quantified and/or the binocular balance is adjusted.

The change in power of the lens may be directly provided as a quantification value of the dominance. Or the change in power may be qualified dominance (strong or light for example). It may be useful to know or give this data to an eye care provider (ECP) to help him/her in case to make a decision for a prescription (for example in case of anisometropia). It may be a decision aid, other than visual acuity.

According to one embodiment, in order to perform the iteration steps, the control unit may execute an adaptive algorithm. The adaptive algorithm is configured to accept a report describing how the subject 4 sees when presented the first image 20L, 30L and the second image 20R, 30R, and to calculate adjustments to the feature values of the first and/or second target 22L, 32L, 22R, 32R on the first image 20L, 30L and the second image 20R, 30R to be presented in a next iteration of the first image 20L, 30L and the second image 20R, 30R according to the report. The next iteration of the first image 20L, 30L and the second image 20R, 30R to the subject 4 is provided by a target-generating component.

Advantageously, adjusting binocular balance allows determining a pair of ophthalmic lenses adapted to a wearer. For that, the steps may be:

- measuring (91 in FIG. 8C) the refraction of each eye of the subject,
- providing (92 in FIG. 8C) a correction based on the measured monocular refraction by adjusting a power lens in front of the first eye and/or the second eye, Then the preceding steps described for the method for adjusting the binocular balance are performed.

Alternatively, the adjustment of the binocular balance may occur at the beginning of the refraction process or before the refraction process, in particular if the refraction is a binocular refraction.

Measuring the refraction of each eye of the subject may be an objective measurement using an auto refractometer or a subjective measurement using a phoropter with monocular steps or binocular refraction.

Accordingly, one object of the present disclosure is a refractometer comprising an apparatus for quantifying ocular dominance of a subject as described in the present disclosure.

In the case where the patient does not suffer from hyperopia, advantageously, by correcting the dominant eye with a blurring lens instead of corrected by increase the optical power of the non-dominant eye, it allows also decreasing the thickness of the lens by at the end to subtract the blurring lens to the measured monocular refraction and thus to decrease the optical power.

The targets may be surrounded as illustrated, for example, in FIGS. 2A, 2B, 2C in order to increase the concentration of the subject on the target.

As explained above in the section presenting a "summary", making use of such first and second images improves the stability of the binocular vision of the subject 4 and makes the observation of these images more comfortable, avoiding blinking or flickering of the global image perceived by the subject (after fusion), and limiting ocular vergence issues. An ocular dominant eye method in which such images are provided to the subject, can thus be carried on faster, and leads to more accurate results.

A first, second, third, fourth and fifth couples of test images, each comprising a first image 30L and a second image 30R having the characteristics mentioned above, are described below (in reference to FIGS. 3A, 3B, 3C, 4A, 4B, 4C, 5A, 5B, 5C, 6A, 6B, 6C, 7A, 7B, and 7C) in the section entitled "images".

According to one embodiment of the apparatus described here, one or several of these couples of images are stored in the memory of the control unit, so that they can be displayed by the display 7 when a ocular dominant method is carried on by means of the apparatus 1 described above. More generally, at least one computer program is stored in the memory of the control unit, this computer program comprising instructions, which, when the program is executed by the control unit 8, cause the apparatus 1 to carry out a method having the features presented above (like the methods described in detail below). This computer program comprises data representative of at least one of these couples of images.

Images

In each exemplary couples of images described below, the first image 30L represents a first target 32L to a first eye 2 of the subject 4, the second image 30R represents a second target 32R to a second eye of the subject 4.

In each exemplary couples of images described below, the first image 30L and the second image 30R are such that the first target 32L on the first image 30L has an identical position, an identical orientation, an identical size and an identical shape to the second target 32R on the second image 30R. As explained above for FIGS. 2A, 2B, 2C, the first target 32L comprises n points (PL1, . . . , PLi, . . . PLj, . . . PLn) and the second target (22R, 32R) comprises n points (PR1, . . . , PRi, . . . PRj . . . PRn) where $n \geq 2$, $1 \leq i \leq n$ and $1 \leq j \leq n$. Each point (PLi) of the first target 32L matches with a point (PRi) of the second target 32R where PLi has the same position in the first image 30L than PRi for $1 \leq i \leq n$ in the second image 30R.

One point may be a pixel of the display.

To each point (PLi) of the first target and to each point (PRi) of the second target corresponds respectively a feature value VLi for the first target and a feature value VRi for the second target. The feature value VLi, VLj of at least two points (PLi, PLj) of the first target differs and for each n points (PLi, PRi) of the first and second target $$VLi+VRi=VLj+VRj \text{ for any } i \text{ and } j.$$

Consequently, the feature value VRi, VRj of the two points (PRi, PRj) of the second target which match with the two points (PLi, PLj) of the first target, differs.

FIGS. 2B, 3B, 4B, 5B, 6B, 7B illustrate the image 30S with the summed up target 32S and as observed, the feature values are constant at each point of the summed up target.

The feature value may be the luminosity as illustrated in FIGS. 2A, 2B, 2C, 3A, 3B, 3C, 4A, 4B, 4C, 6A, 6B, 6C, 7A, 7B, 7C. Thus the feature value of the target may correspond to a level of grey or to an intensity or an amplitude for a same color. This embodiment presents the advantage to avoid issues related to color blindness because the different feature values do not correspond to different colors.

Alternatively, the feature value may be the color (not shown).

Each of the first and second images to be displayed may comprises:

- a central image with a target, and optionally
- a peripheral image that surrounds the central image and contributes usefully to a well-balanced fusion process between the left and right visual pathway, for the subject.

So, the images may be somehow composite images, and, besides, they comprise a peripheral image that is all the more stabilizing as the part of the field of view it occupies is wide. It is thus very useful to use a wide screen, as the one described above, to provide enough room to accommodate such composite images.

The FIGS. 2A, 2B, 2C and 6A, 6B, 6C show images with an uniform peripheral image. Alternatively, the FIGS. 3A, 3B, 3C, 4A, 4B, 4C, 5A, 5B, 5C and 7A, 7B, 7C present a rich and diversified content of the peripheral image.

Advantageously, the rich and diversified visual content of the first peripheral image contributes to the stabilizing effect of this image. Indeed, it provides an abundant visual support, identical or similar to the one present in the second peripheral image, which enables a very stable and well-balanced fusion between the left and right visual pathways of the subject. It helps focusing and fusion because the 3D scene may bring elements of perception for monocular and binocular distances, which enable the visual system to stabilize. Besides, it captures the attention of the subject, from a visual point of view and helps maintaining the subject focused on the test images provided to him/her.

According to an embodiment, the peripheral image may be:

- abundant scenes,
- with 3D (perspectives),
- natural scenes
- stereoscopy (plus or minus disparities)

Figure 3A:
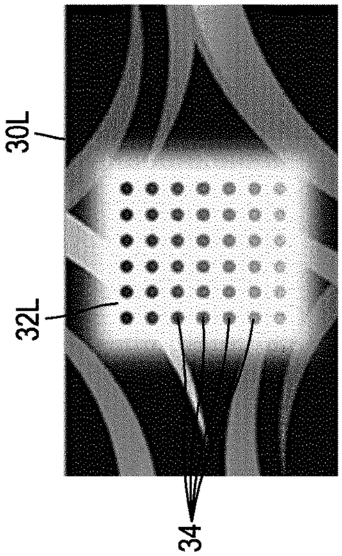
Figure 3B:
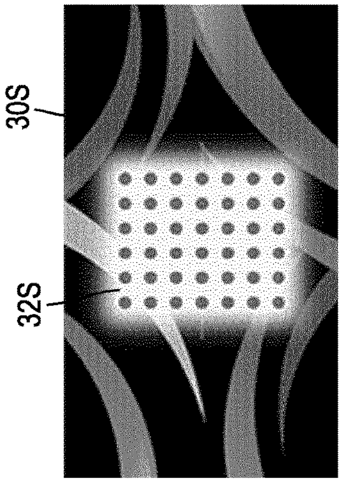
Figure 3C:
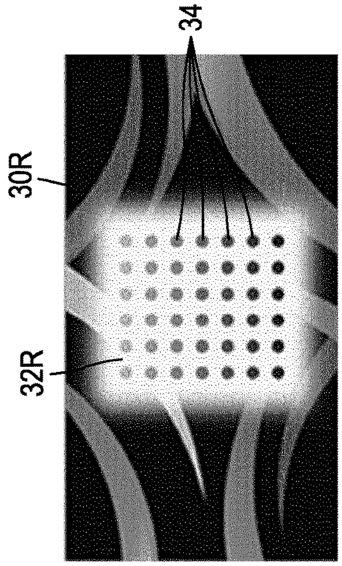
Figure 5A:
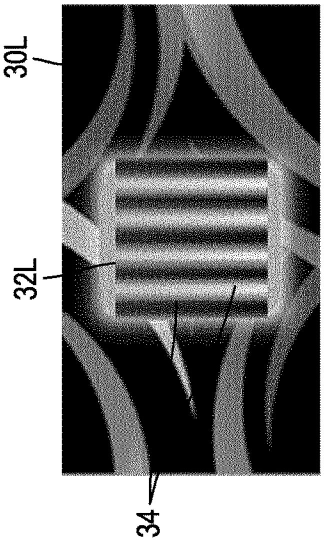
Figure 5B:
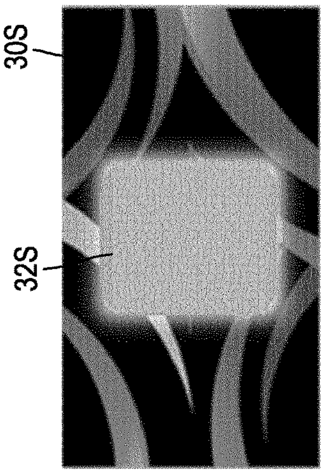
Figure 5C:
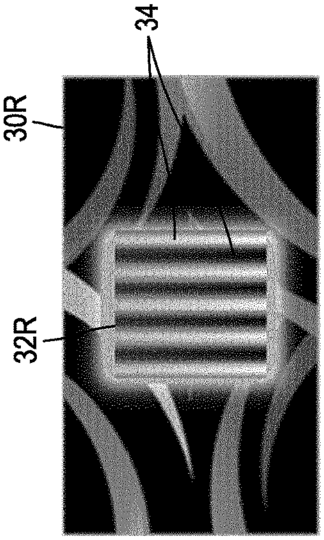
Figure 6A:
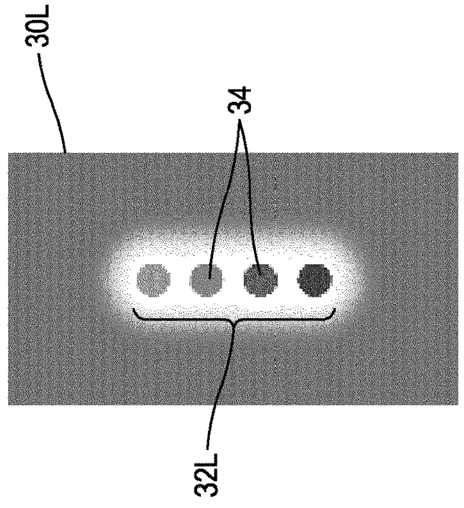
Figure 6B:
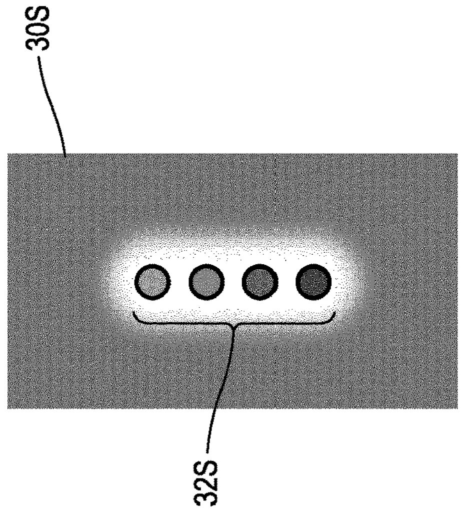
Figure 6C:
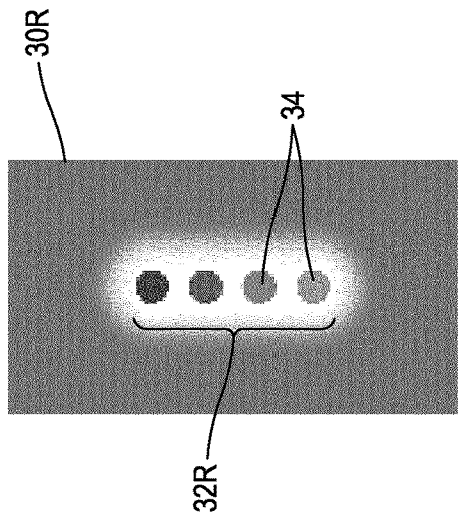
Figure 7A:
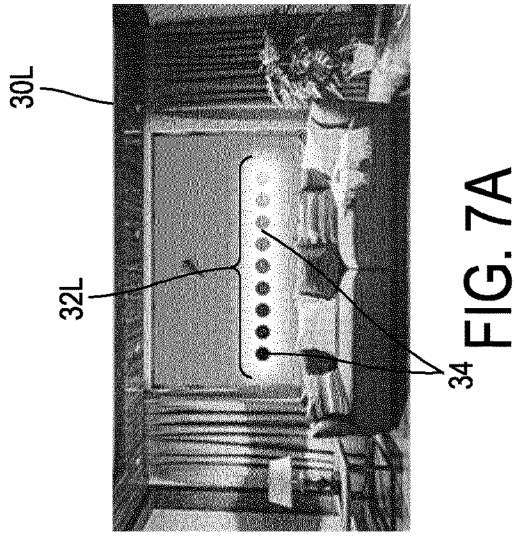
Figure 7B:
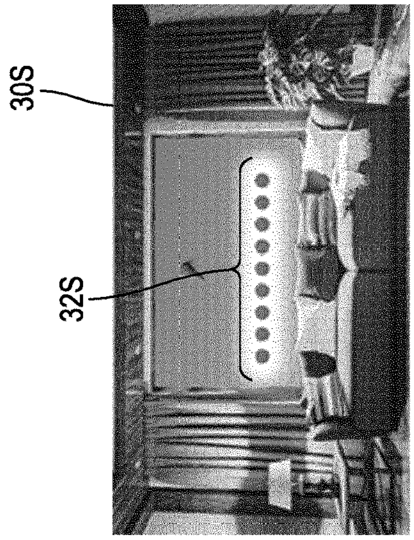
Figure 7C:
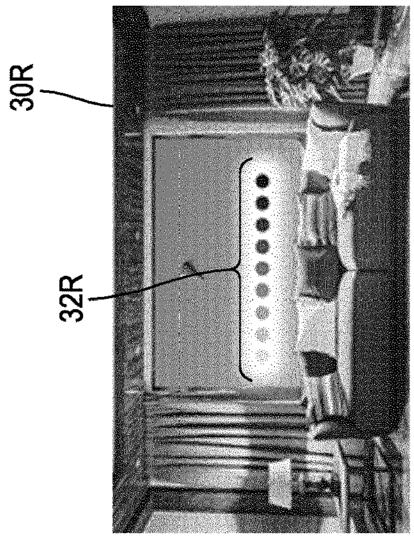

The shape of the targets 22L, 32L, 22R, 32R may be:

- an element grid comprising at least three elements, the at least three elements having the same shape and the same size. For example, the FIGS. 3A, 3B, 3C illustrate targets being an element grid comprising a matrix of six by six elements 34.
- an element line comprising at least three elements, the at least three elements having the same shape and the same size. For example, the FIGS. 2A, 2B, 2C and 7A, 7B, 7C illustrate targets being an element line comprising four elements 24 in FIGS. 2A, 2B, 2C and nine elements 24 in FIGS. 7A, 7B, 7C; the peripheral image is uniform on FIGS. 2A, 2B, 2C and rich on FIG. 7A, 7B, 7C as representing a house interior.
- an element column comprising at least three elements, the at least three elements having the same shape and the same size. For example, the FIGS. 6A, 6B, 6C illustrate targets being an element column comprising four elements 34.
- at least two fringes. The fringes may be horizontal or vertical. For example, the FIGS. 5A, 5B, 5C illustrate targets being a set of nine vertical fringes, which alternate between dark fringes and white fringes.
- letter(s) or optotype(s) or figure(s). For example, the FIGS. 4 illustrate targets being a set of letters on an uniform background.

The element may be a square, a circle, a star, an animal or any other kind of shape.

The figure may be a square, a circle, a star, an animal, an object or any other kind of shape.

Figure 4A:
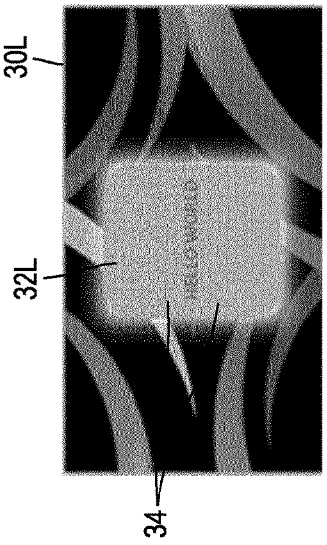
Figure 4B:
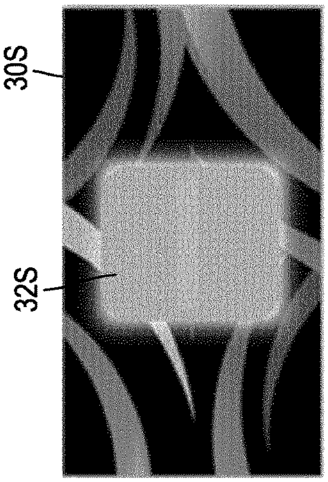
Figure 4C:
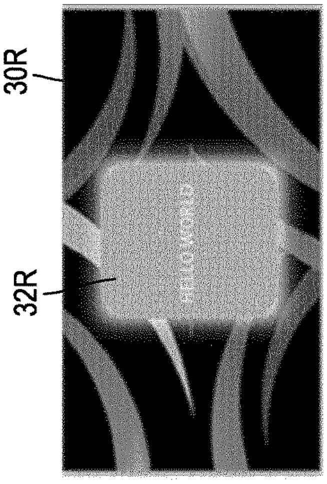

Optionally, the target may comprise an uniform background as illustrated in FIGS. 4A, 4B, 4C, or not comprise an uniform background as illustrated for example in FIGS. 3A, 3B, 3C.

The feature values of the uniform background may be an average (VLi, VRi) or may any other constant value.

Optionally, the central image may comprise the target and a background as illustrated on FIGS. 2A, 2B, 2C, 3A, 3B, 3C, 6A, 6B, 6C, 7A, 7B, 7C with for example a white background in order to highlight the target.

Besides, in each couple of images described above, instead of being identical, the first and second peripheral images could be such that, when the first and second images are superimposed to each other (with their respective frames coinciding with each other), some elements of the first peripheral image are slightly side-shifted with respect to the corresponding elements of the second peripheral image, to enable a 3-D stereoscopic rendering of the scene represented. More precisely, in such a case, the first peripheral image would represent an actual scene, object, or abstract figure as it would be seen from the position of the first eye 2 of the subject, while the second peripheral image would represent to the same scene, object or abstract figure, as it would be seen from the position of the second eye 3 of the subject.

Employing such stereoscopic images is a very efficient way to get rid of the suppression phenomenon described in the preamble. Indeed, with such test images, the subject has a very strong tendency to try to perceive the scene in a 3-dimensional manner, and thus takes into account both the left and right visual pathway in the fusion process (thus eliminating the "suppression phenomenon"), to obtain this 3-dimensional rendering. When such stereoscopic images are employed, the way to compute their level of similarity has to be adapted, to take into account their 3-dimensional nature.

The examples of FIGS. 2A, 2B, 2C, 3A, 3B, 3C, 6A, 6B, 6C and 7A, 7B, 7C work very similarly because in these fourth embodiments, the target is a set of dots positioned horizontally, vertically or in matrix.

In the example of FIGS. 4A, 4B, 4C, using letters, the first target 32L has a grey background and darker letters, the second target 32R has a grey background and lighter letters identical to the first target. A right dominant eye will get the user perceive the text with a brighter level (white letter/grey background). A left dominant eye will get the user perceive the text with a darker level (dark text/grey background). Balance will make the text very difficult to perceive.

In the example of FIGS. 5A, 5B, 5C, the first target 32L is a set of nine vertical fringes, which alternates between dark fringes and white fringes. The second target 32R has identical shape but has Pl phase shift. Optionally, in this case, spatial frequency may be selected in order to have low spatial frequency, lower than eye resolution (period >>1' arc). Thus, when binocular vision is balanced, the user will perceive the fringes with minimum contrast. When binocular vision is not balanced, the fringes will be perceived with higher contrast. Optionally, the fringes may be temporally oscillating to improve visibility.

Optionally, the target may be surrounded with a peripheral area as illustrated in FIGS. 2A, 2B, 2C, 3A, 3B, 3C, 6A, 6B, 6C and 7A, 7B, 7C in order to increase the concentration and the facility of the observation of the target.

Optionally, the feature value inside each element of the target are constant but different between at least two elements. This embodiment allows to make easier to the subject to describe the position of the feature values.

The method and images used in the apparatus of the present disclosure may use interactive elements or steps. A keyboard or pad may be used to input the answers of the subject or to enable the subject to go back to previous scenes if he/she wishes to. An indicator may be used to display graphically the degree of advancement of the method. Explanations on the test and/or a playful, nice story telling explaining the test and focusing on some objects that will be shown during the test (treasure hunt like test) may be given at the beginning of the tests in order to get attention, cooperation and understanding of tests (questions/answers) from the subject and above all to make sure that the subject is not stressed during the visual examination.

Although representative methods, apparatus and set of images have been described in detail herein, those skilled in the art will recognize that various substitutions and modifications may be made without departing from the scope of what is described and defined by the appended claims.

What is claimed is:

1. An apparatus for quantifying ocular dominance of a subject comprising:

at least one display to display a first image representing a first target to a first eye of the subject, and to display a second image representing a second target to a second eye of the subject; and processing circuitry configured to control the at least one display, wherein the first image and the second image are such that the first target on the first image has an identical position, an identical orientation, an identical size and an identical shape to the second target on the second image;

the first target comprises n points and the second target comprises n points where n≥3, the n points of the first target having a same shape and a same size as the n points of the second target, and the n points of the first target having a different phase shift from the n points of the second target;

each point PLi of the first target matches with a point PRi of the second target where point PLi has a same position in the first image as point PRi in the second image where 1≤i≤n;

to each point of the first target and to each point of the second target corresponds respectively a feature value VLi for the first target and a feature value VRi for the second target;

feature values of the at least three points of the first target, which have the same shape and the same size as the points of the second target and which have the different phase shift from the points of the second target, differ such that an intensity of the feature values, of the at least three points of the first target, gradually increases between each of the at least three points of the first target, and such that an intensity of the feature values, of the at least three points of the second target, gradually decreases between each of the at least three points of the second target; and for two points of the first target having feature values VLi and VLj, respectively, and two points of the second target having feature values VRi and VRj, respectively, VLi+VRi=VLj+VRj for any i and j where 1≤j≤n.

2. The apparatus according to claim 1, further comprising:

a first optical unit and a second optical unit respectively in front of the first eye and in front of the second eye of the subject, and a power modulator to change an optical power of the optical unit in front of each eye, the power modulator being controlled by the processing circuitry.

3. The apparatus according to claim 1, wherein feature values of a target are luminosity or color, and when the feature values are colors, VLi+VRi is a same color as VLj+VRj.

4. The apparatus according to claim 1, wherein the shape of the targets is:
- an element grid comprising at least three elements, the at least three elements having the same shape and the same size,
- an element line comprising at least three elements, the at least three elements having the same shape and the same size,
- an element column comprising the at least three elements, the at least three elements having the same shape and the same size,
- at least two fringes,
- letter(s),
- optotype(s), or
- figure(s).

5. The apparatus according to claim 1, wherein the processing circuitry is further configured to execute an adaptive algorithm
- to accept a report describing how the subject sees when presented the first image and the second image,
- to calculate adjustments of the feature values of the first and/or second target on the first image and the second image to be presented in a next iteration of the first image and the second image according to the report, and
- to display the next iteration of the first image and the second image to the subject.

6. The apparatus according to claim 2, wherein the processing circuitry is further configured to execute an adaptive algorithm
- to accept a report describing how the subject sees when presented the first image and the second image, and
- to calculate adjustments of the optical power of the optical units in a next iteration of the first image and of the second image according to the report.

7. A refractometer comprising the apparatus for quantifying ocular dominance of a subject according to claim 1.

8. The apparatus according to claim 1, wherein
- feature values of a target are luminosity,
- the intensity of the feature values gradually increases from dim light to bright light, and
- the intensity of the feature values gradually decreases from bright light to dim light.

9. A device comprising:
- processing circuitry configured to control display of a set of images for quantifying ocular dominance of a subject, the set of images including a first image representing a first target and a second image representing a second target, wherein:
- the first image and the second image are such that the first target on the first image has an identical position, an identical orientation, an identical size and an identical shape to the second target on the second image;
- the first target comprises n points and the second target comprises n points where n≥3, the n points of the first target having a same shape and a same size as the n points of the second target, and the n points of the first target having a different phase shift from the n points of the second target;
- each point PLi of the first target matches with a point PRi of the second target where point PLi has a same position in the first image as point PRi in the second image where 1≤i≤n;
- to each point of the first target and to each point of the second target corresponds respectively a feature value VLi for the first target and a feature value VRi for the second target;
- feature values of the at least three points of the first target, which have the same shape and the same size as the points of the second target and which have the different phase shift from the points of the second target, differ such that an intensity of the feature values, of the at least three points of the first target, gradually increases between each of the at least three points of the first target, and such that an intensity of the feature values, of the at least three points of the second target. gradually decreases between each of the at least three points of the second target; and
- for two points of the first target having feature values VLi and VLj, respectively, and two points of the second target having feature values VRi and VRj, respectively, VLi+VRi=VLj+VRj for any i and j where 1≤j≤n.

10. A method for quantifying ocular dominance of a subject comprising:
- displaying a first image to a first eye of the subject, the first image representing a first target;
- displaying a second image to a second eye of the subject, the second image representing a second target;
- checking that the subject sees a fused image from the first image and the second image, the fused image comprising a fused target with feature values;
- generating a first report describing the features values of the fused image; and
- determining which eye is a dominant eye of the subject based on the first report, wherein
- the first image and the second image are such that the first target on the first image has an identical position, an identical orientation, an identical size and an identical shape to the second target on the second image;
- the first target comprises n points and the second target comprises n points where n≥3, the n points of the first target having a same shape and a same size as the n points of the second target, and the n points of the first target having a different phase shift from the n points of the second target;
- each point PLi of the first target matches with a point PRi on the second target where point PLi has a same position in the first image as point PRi in the second image, where 1≤i≤n;
- to each point of the first target and to each point of the second target corresponds respectively a feature value VLi for the first target and a feature value VRi for the second target;
- feature values of the at least three points of the first target, which have the same shape and the same size as the points of the second target and which have the different phase shift from the points of the second target, differ such that an intensity of the feature values, of the at least three points of the first target, gradually increases between each of the at least three points of the first target, and such that an intensity of the feature values, of the at least three points of the second target, gradually decreases between each of the at least three points of the second target; and
- for two points of the first target having feature values VLi and VLj, respectively, and two points of the second target having feature values VRi and VRj, respectively, VLi+VRi=VLj+VRj for any i and j where 1≤j≤n.

11. The method according to claim 10, further comprising after determining which eye is the dominant eye of the subject:

calculating adjustments to the feature values of the first and/or second target on the first image and the second image to be presented in a next iteration of the first image and the second image according to the report;

displaying the next iteration of the first image and the second image with the adjusted feature values;

generating a second report describing how the subject sees the features values of the fused target from the next iteration of the first image and of the second image;

repeating the calculating the adjustments, the displaying the next iteration, and the generating the second report until the subject indicates that the feature values of the fused target of the fused image are constant at each point of the fused target of the fused image; and quantifying ocular dominance of the subject based on the reports of the subject.

12. The method according to claim 10, wherein the shape of the targets is a set of at least three elements, said at least three elements having the same shape and the same size, wherein the feature values of the target are luminosity, and wherein the first report describes a location of a brightest and/or darkest element of the fused target of the fused image.

13. The method according to claim 10, wherein the target is a set of at least three elements, said at least three elements having the same shape and the same size, wherein the feature values of the target are colors of the target, $$VLi+VRi=VLj+VRj$$

meaning that VLi corresponds to a first color and VLj corresponds to a second color which is a complementary color of the first color and VLi+VRi is a same color as VLj+VRj, and wherein the reports describe a location of the colors on the fused target of the fused image.

14. The method according to claim 10, wherein the fused image is a 3-D stereoscopic image.

15. A method for adjusting a binocular balance of a subject comprising:

displaying a first image to a first eye of the subject, the first image representing a first target;

displaying a second image to a second eye of the subject, the second image representing a second target;

checking that the subject sees a fused image from the first image and the second image, the fused image comprising a fused target with feature values;

generating a report describing the features values of the fused image;

determining which eye is a dominant eye of the subject based on the report; and providing a correction to the dominant eye of the subject by adjusting a power lens in front of the first eye and/or the second eye until the feature values of the fused image are constant for the subject, wherein the first image and the second image are such that the first target on the first image has an identical position, an identical orientation, an identical size and an identical shape to the second target on the second image, the first target comprises n points and the second target comprises n points where $n \geq 3$, the n points of the first target having a same shape and a same size as the n points of the second target, and the n points of the first target having a different phase shift from the n points of the second target;

each point PLi of the first target matches with a point PRi on the second target where point PLi has a same position in the first image as point PRi in the second image where $1 \leq i \leq n$;

to each point of the first target and to each point of the second target corresponds respectively a feature value VLi for the first target and a feature value VRi for the second target;

feature values of the at least three points of the first target, which have the same shape and the same size as the points of the second target and which have the different phase shift from the points of the second target, differ such that an intensity of the feature values, of the at least three points of the first target, gradually increases between each of the at least three points of the first target, and such that an intensity of the feature values, of the at least three points of the second target, gradually decreases between each of the at least three points of the second target; and for two points of the first target having feature values VLi and VLj, respectively, and two points of the second target having feature values VRi and VRj, respectively, VLi+VRi=VLj+VRj for any i and j where $1 \leq j \leq n$.

16. The method for adjusting a binocular balance of a subject according to claim 15, further comprising:

measuring a refraction of each eye of the subject; and providing a correction based on the measured refraction by adjusting a power lens in front of the first eye and/or the second eye.

* * * * *